(12) United States Patent
Shapiro

(10) Patent No.: US 8,770,010 B1
(45) Date of Patent: Jul. 8, 2014

(54) INTEGRATED DETECTOR FOR DETECTING BUBBLES IN FLUID FLOW AND OCCLUSIONS IN A TUBE

(75) Inventor: Daniel Shapiro, Branford, CT (US)

(73) Assignee: Strain Measurement Devices, Inc., Wallingford, CT (US)

( * ) Notice: Subject to any disclaimer, the term of this patent is extended or adjusted under 35 U.S.C. 154(b) by 269 days.

(21) Appl. No.: 12/798,032

(22) Filed: Mar. 29, 2010

Related U.S. Application Data

(60) Provisional application No. 61/211,450, filed on Mar. 30, 2009.

(51) Int. Cl.
*G01M 3/02* (2006.01)
(52) U.S. Cl.
USPC .................................................. 73/37
(58) Field of Classification Search
USPC .............................................. 73/37
See application file for complete search history.

(56) References Cited

U.S. PATENT DOCUMENTS

| 4,607,520 A | 8/1986 | Dam ................................. 73/19 |
| 5,395,320 A * | 3/1995 | Padda et al. ..................... 604/65 |
| 6,773,412 B2 | 8/2004 | O'Mahony et al. .......... 604/5.01 |
| 7,121,143 B2 | 10/2006 | Malmstrom et al. ............ 73/705 |
| 2008/0134750 A1 * | 6/2008 | Riley et al. ................... 73/19.03 |

* cited by examiner

*Primary Examiner* — Peter Macchiarolo
*Assistant Examiner* — Alex Devito
(74) *Attorney, Agent, or Firm* — Fattibene and Fattibene LLC; Paul A. Fattibene

(57) ABSTRACT

An integrated fluid sensor combining bubble and occlusion detection. A housing having a channel with three sides holds a tube containing a fluid flow. An ultrasonic transmitter and ultrasonic receiver retain the tube on two opposing sides. Placed between the two opposing sides is a third side containing a pressure sensor. The pressure sensor contacting the surface of the tube detects changes of pressure within the tube due to changes in fluid flow so as to detect occlusions. The restraining of the tube between the opposing ultrasonic transmitter and ultrasonic receiver confine the tube so that a resulting increase in pressure is detected by the pressure sensor. A reduction in the size of devices for detecting fluid flow or bubbles is made possible.

8 Claims, 5 Drawing Sheets

INTEGRATED DETECTOR FOR DETECTING BUBBLES IN FLUID FLOW AND OCCLUSIONS IN A TUBE

RELATED APPLICATION

This application claims the benefit of U.S. Provisional Application No. 61/211,450 filed Mar. 30, 2009.

FIELD OF THE INVENTION

The present invention relates in general to detectors, and particularly to a detector for detecting bubbles in fluid flow and occlusions in a conduit or tube.

BACKGROUND OF THE INVENTION

There are many applications where accurate detection of fluid flow is required. For example, in many medical devices the flow of body fluids, including blood, needs to be detected accurately. Some additional applications include infusion pumps, insulin pumps, enteral feed pumps, and wound irrigations systems, among others. Often, it is critical that any air bubbles or interference with fluid flow, such as by occlusions, within the conduit or tube must be quickly and accurately detected.

Different systems have been incorporated in medical devices to detect bubbles in a fluid stream. Often, ultrasonic energy is used to detect bubbles in fluid flowing in a tube. One such device is disclosed in U.S. Pat. No. 4,607,520 entitled "Method and Apparatus for Detecting Discontinuity in a Fluid Stream", and issuing to Dam on Aug. 26, 1986. Therein disclosed is a device for detecting discontinuities such as air bubbles in a fluid stream. A tube containing the fluid stream is positioned between a transducer transmitting ultrasonic energy and a receiver receiving the transmitted ultrasonic energy upon passing through the tube and fluid stream. Signal processing circuits detect any modification of the ultrasonic energy indicating a discontinuity or bubble within the fluid stream. While this device is suitable for detecting bubbles or discontinuities in a fluid stream, it is not able to detect whether or not an occlusion or restriction to the flow of the fluid exists or that there has been a reduction in the fluid flow.

Other devices have been used to optically detect pressure changes in a tube that may be indicative of an occlusion or other restriction in the fluid flow. One such device is disclosed in U.S. Pat. No. 7,121,143 entitled "Optical Pressure Monitoring System" and issuing to Malmstrom et al on Oct. 17, 2006. Therein disclosed is a tube placed between an optical signal emitter and an optical signal receiver. The tube is formed from a generally elastomeric material, such as silicone. Accordingly any occlusion or viscosity increase will increase pressure, causing the tube to expand and move a portion of the tube between the optical signal emitter and the optical signal receiver which is optically detected. While this device is acceptable in many applications for detecting occlusions or a change in the fluid flow, it requires an optical signal emitter and an optical signal receiver to be placed on either side of the tube, making the device relatively large and difficult to implement efficiently in different applications.

In many applications both the detection of bubbles and the detection of fluid flow or changed due to an occlusion is necessary. This is especially applicable in medical devices used to monitor and detect blood flow. One such device is disclosed in U.S. Pat. No. 6,773,412 entitled "User Interface for Blood Treatment Device", issuing to O'Mahony et al on Aug. 10, 2004. Therein disclosed is a renal replacement therapy device using fluid lines, pumps and sensors used for renal replacement therapy. Separate blood pressure sensors are used as well as an air detector circuit using ultrasound waves in a fluid to detect air bubbles in the blood passage. Use of these multiple, separate sensors, that are relatively large and cumbersome, make it difficult to develop small devices.

Accordingly, there is an increasing need for providing small, compact, easily transported or disposable devices in the medical field that can accurately and easily detect fluid flow and bubble. Therefore there is a need to produce easily manufactured sensors that can incorporate multiple functions in a single device and in a compact package.

SUMMARY OF THE INVENTION

The present invention provides an integrated sensor or detector for detecting both air bubbles and occlusion in fluid flowing in a tube. A housing has a channel therein formed by an ultrasonic transmitter and an opposing ultrasonic receiver used for detecting discontinuities or bubbles in a fluid flow. On a bottom surface, between the ultrasonic transmitter and ultrasonic receiver, is a pressure sensor positioned to contact the tube containing the fluid flow. Accordingly the pressure sensor need only contact the tube at one location between the ultrasonic transmitter and the ultrasonic receiver. With the tube confined between the ultrasonic transmitter and the ultrasonic receiver, within the channel and adjacent the pressure sensor, any changes in fluid flow or occlusion will result in an increase in pressure applied to the pressure sensor permitting detection.

Accordingly it is an object of the present invention to provide an integrated detector for detecting both bubbles and occlusions in a fluid flow.

It is another object of the present invention to reduce the space required for incorporating separate detectors in a device.

It is an advantage of the present invention that a compact integrated detector is formed.

It is yet another advantage of the present invention that an occlusion detector can be utilized with no additional space than that required for a bubble detector.

It is a feature of the present invention that an ultrasonic bubble detector and a pressure sensor occlusion detector are combined in a single space-saving device.

It is another feature of the present invention that a housing has a curved surface adjacent a channel for receiving a tube.

These and other objects, advantages, and features will become more readily apparent in view of the following detailed description.

BRIEF DESCRIPTION OF THE DRAWINGS

FIG. 4b is a cross section elevational view taken along line A-A of FIG. 4a.

FIG. 5b is an elevational view of the force or pressure sensor insert illustrated in FIG. 5a.

BRIEF DESCRIPTION OF THE PREFERRED EMBODIMENTS

Figure 1:
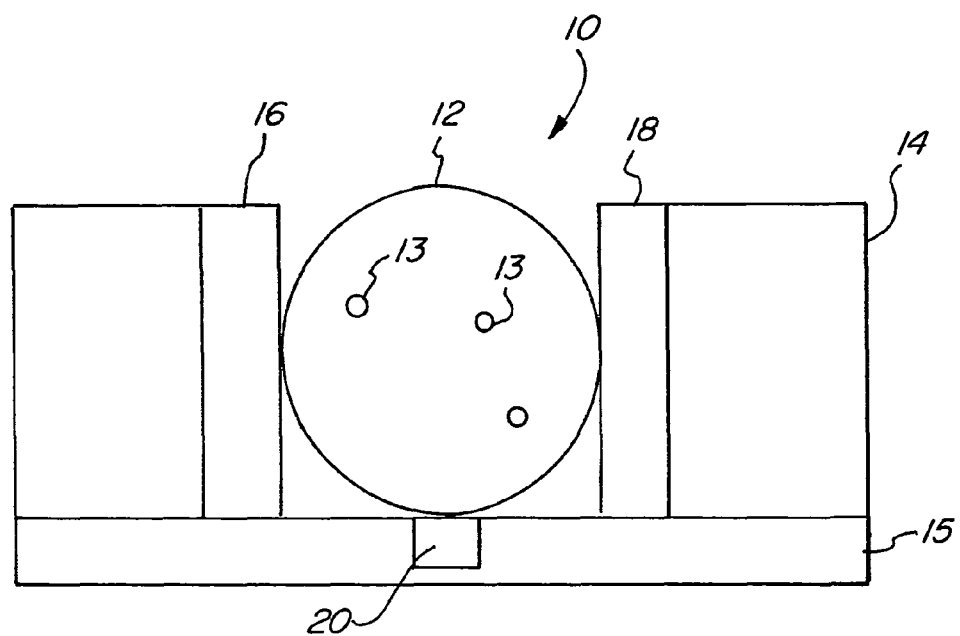
FIG. 1 schematically illustrates the present invention.

FIG. 1 schematically illustrates a fluid sensor or detector of the present invention that is able to detect bubbles and occlusions within fluid flowing in a tube or conduit. The fluid sensor 10 holds a tube 12 having fluid flow. Bubbles 13, which are to be detected, may sometimes be present in the fluid flow. A housing 14 holds an ultrasonic transmitter 16 and ultrasonic receiver 18 with the tube 12 placed there between. Suitable electronics may also be contained in the housing 14 for operating the ultrasonic transmitter 16 and ultrasonic receiver 18. The ultrasonic transmitter 16 and ultrasonic receiver 18 may be similar to those disclosed in U.S. Pat. No. 4,607,520 issued Aug. 26, 1986 to Dam and entitled "Method and Apparatus for Detecting Discontinuities in a Fluid Stream", which is herein incorporated by reference. In a bottom portion 15 of housing 14 and positioned under tube 12 is placed a force or pressure sensor 20. The force or pressure sensor 20 detects force or pressure developing on the wall of the tube 12 so as to detect any restriction in fluid flow or occlusion within the tube 12. The force or pressure sensor 20 may be a thin film sensor. Additionally, the force or pressure developed within the tube 12 due to a restriction or occlusion may be optically measured. An optical system is disclosed in U.S. Pat. No. 7,121,143 issued Oct. 17, 2006 to Malmstrom et al and entitled "Optical Pressure Monitoring System", which is herein incorporated by reference.

Figure 2:
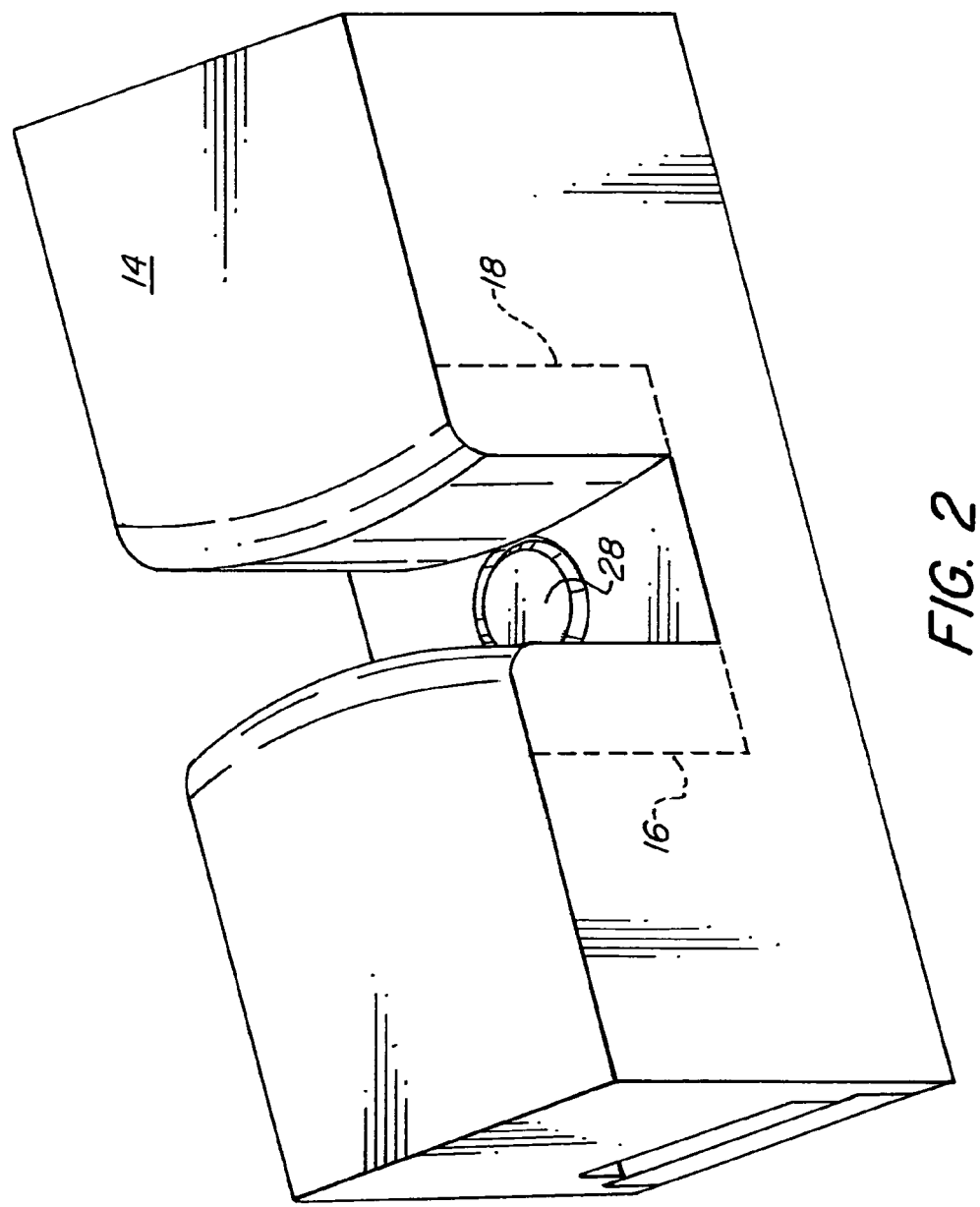
FIG. 2 is a perspective view illustrating an embodiment of the present invention.

FIG. 2 is a perspective view illustrating the present invention. Housing 14 has a central channel adapted to hold a tube. A force or pressure sensor load button 28 is placed at the bottom of the central channel. The load button 28 is coupled to a force or pressure sensor or detector. The ultrasonic transmitter 16 and ultrasonic receiver 18 are placed adjacent each side wall of the central channel.

Figure 3:
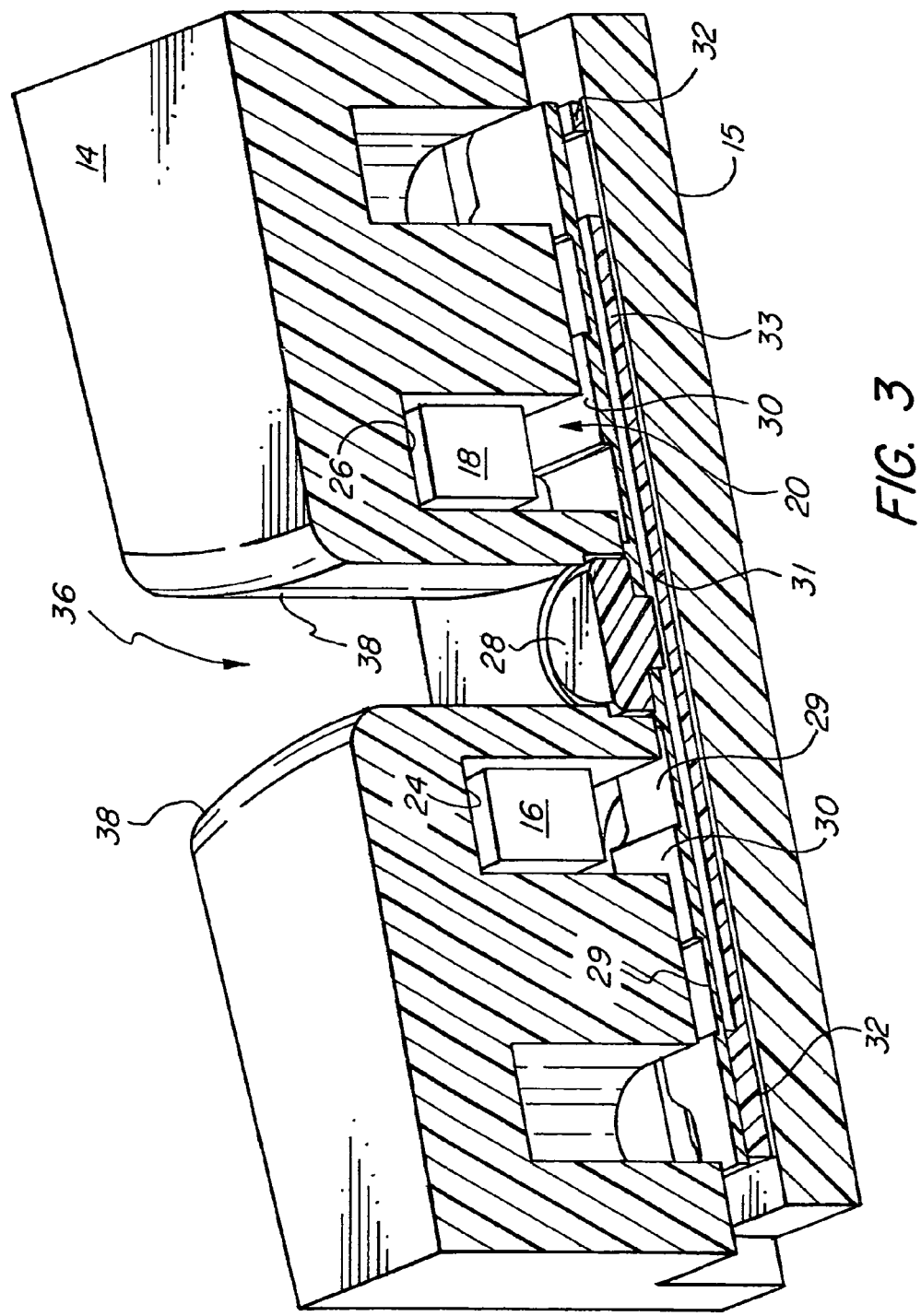
FIG. 3 is a cut away perspective view illustrating the embodiment of the invention illustrated in FIG. 2.

FIG. 3 is a perspective cross section illustrating the present invention. Housing 14 is connected to bottom or base 15. Placed within opposing chambers 24 and 26 of the housing 14 are the ultrasonic transmitter 16 and ultrasonic receiver 18. The force or pressure sensor insert 20 is attached to the bottom or base 15. The force or pressure sensor insert 20 comprises a pressure sensor load button 28, a thin film strain gauge sensor 30 on either side of said pressure sensor load button connected by webs 29, and a sensor support 32 at either end of the pressure sensor insert 20. The sensor supports 32 are formed on an elongated insert base 33 and support either end of said pressure sensor insert 20. A tube or conduit, not shown, is placed between the ultrasonic transmitter 16 and ultrasonic receiver 18 and is placed in contact with the pressure sensor load button 28. A pre-load or pre-compression may be placed on the tube when inserted in the channel 26. The channel has opposing curved sides 38 that provide a predetermined width therebetween. Expansion of the tube walls due to a pressure change, caused by an occlusion, is transferred to the pressure sensor load button 28 and measured by the strain gauge sensors 30 of the force or pressure sensor 20 insert. The pressure sensor load button 28 is forced downward into the space 31 causing a strain in the strain gauge sensors 30 resulting in a electrical signal proportional to the pressure change. Tube material having low creep is preferred, such as silicone tubing.

Figure 4A:
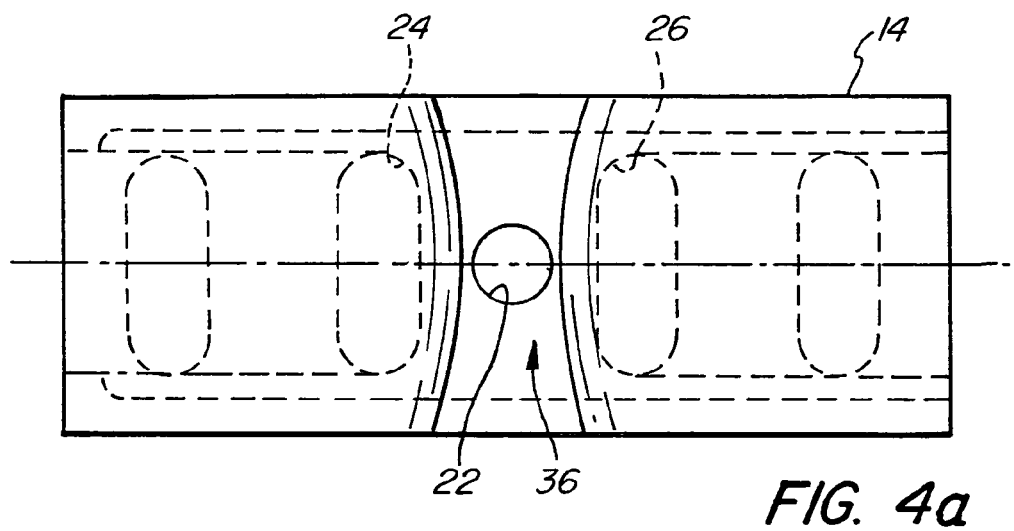
FIG. 4a is a plan view of a housing for the detector of the present invention.
Figure 4B:
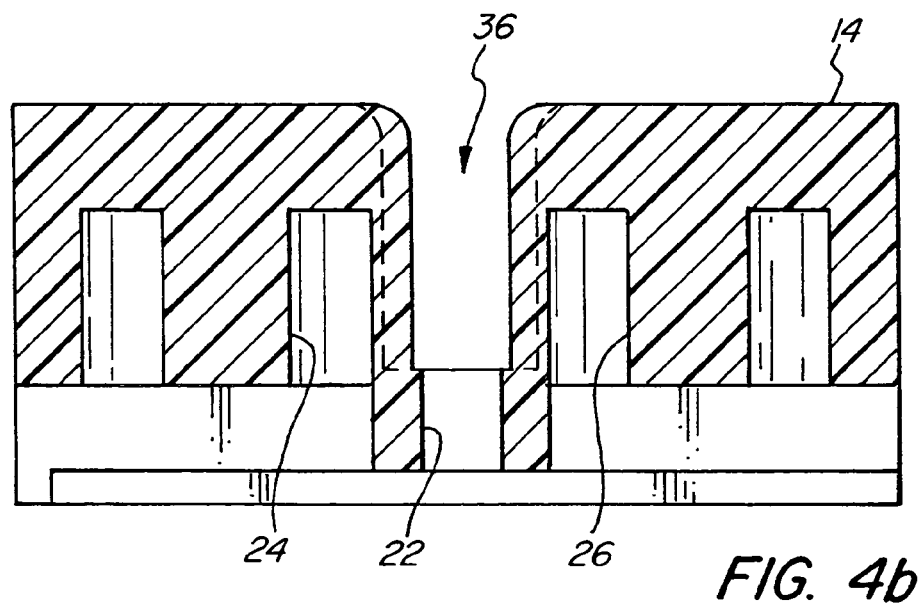

FIGS. 4a and 4b illustrate housing 14 in greater detail. Housing 14 has chambers 24 and 26 formed therein to hold the ultrasonic transmitter 16 and ultrasonic receiver 18, not illustrated. The housing 14 also has a bore 22 for receiving or holding the load button 28, not illustrated. Channel 36 is formed within the housing 14 and has a slight curve with a narrow center portion to better hold a conduit or tubing, not illustrated.

Figure 5A:
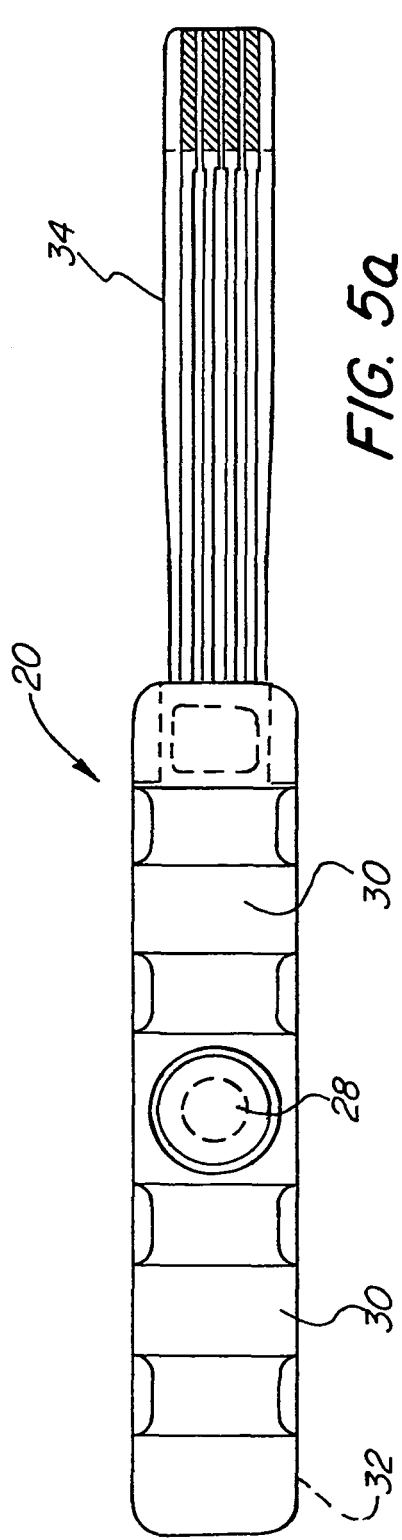
FIG. 5a is a plan view of a force or pressure sensor insert.
Figure 5B:
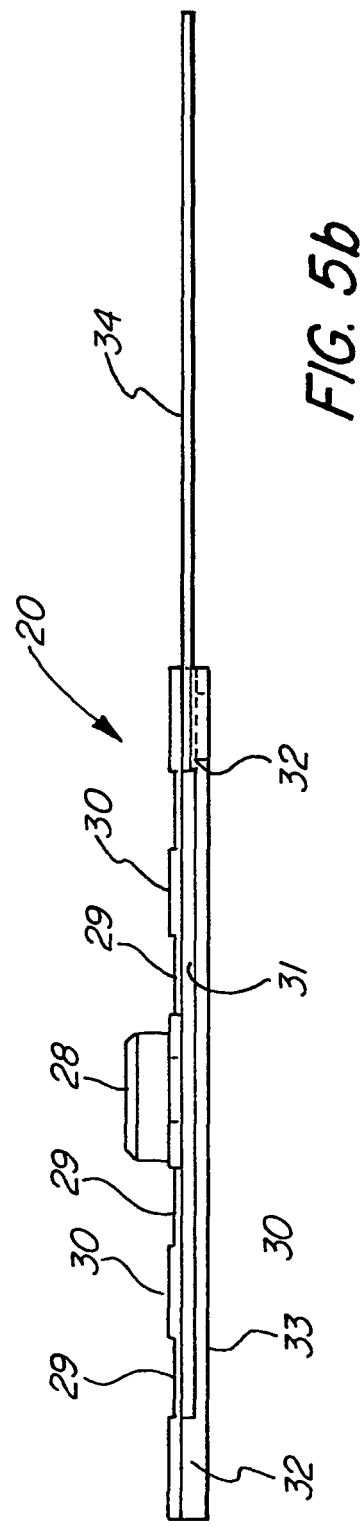

FIGS. 5a and 5b illustrate a thin film force or pressure sensor 20 in the form of an insert that is placed within the housing 14, illustrated in FIGS. 4a and 4b. A sensor 30 is coupled to the load button 28 so that when a load is applied to the load button 28, from the conduit or tubing not shown, a force and slight displacement is detected by the sensor 30. Sensor 30 may be a strain gauge, as is preferably a thin-film sensor. Thin-film strain gauge sensors may be formed by deposition of thin films of dielectric and resistor alloy onto metal components, with the strain-gauge layout formed by laser-cutting to form the load cells and pressure sensor. The layout may be a resistive network or bridge in the form of a Wheatstone bridge. The use of a thin-film sensor has advantages over other devices, due to their rugged nature, small size, and efficient manufacture. The sensor 30 may be supported by a sensor support 32 at either end. A web 29 extends between the sensor supports 32, the sensors 30, and the load button 28. When a pressure or load is placed on the load button 28 the load button 28 is displaced downward slightly into a space 31 placing a strain on the sensors 30. The strain on sensors 30 results in an electrical signal that is proportional to the force applied to the load button 28. Wires 34 transmit the electrical signal to other electronics for analysis or display.

A pre-load or pre-compression may be applied to the tube 12 upon insertion into the channel 36 in the housing 14. The channel 36 may be made of a width to accommodate different size tubes made of different materials. A pre-load or pre-compression applied to the tube 12 based upon a characterization of samples of tubes required for a particular application has greatly increased accuracy that is achieved across a range of different tube materials. Accuracies within a range of approximate 15% have been achieved across a range of different tube materials, and as high as approximately 5% for a single tube material.

In operation, bubbles that may flow in the tube 12 are detected by the ultrasonic transmitter 16 and ultrasonic receiver 18. If sufficient bubbles are detected fluid flow can be stopped or other corrective action taken. Similarly, if the force or pressure sensor insert 20 detects a change in the tube due to a restriction or occlusion this can be detected and corrective action taken.

The present invention provides a compact device that can detect both occlusions and bubbles in a fluid flow or stream. Therefore, the present invention is useful in many applications such as in medical devices that have a critical need for reliable delivery of fluids to the body, such as infusion pumps, insulin pumps, irrigation systems, and other similar devices. The present invention makes possible more compact and reliable devices that improve the delivery of medical services, while reducing cost.

Although the preferred embodiments have been illustrated and described, it will be obvious to those skilled in the art that various modifications may be made without departing from the spirit and scope of this invention.

What is claimed is:

1. A compact sensor for detecting bubbles and occlusions in a fluid flow comprising:
    a housing having a channel with a bottom and opposing curved sides, the opposing curved sides having a narrowest portion adapted to receive and provide a pre-load to a tube;
    a bubble sensor having an ultrasonic transmitter and an ultrasonic receiver, the ultrasonic transmitter and the ultrasonic receiver placed adjacent a respective one of the opposing curved sides in said housing, whereby the ultrasonic transmitter and the ultrasonic receiver are separated by the narrowest portion of the channel; and
    an occlusion sensor placed at the bottom of the channel between the ultrasonic transmitter and the ultrasonic receiver and the opposing curved sides and adjacent and between the narrowest portion of the opposing curved sides in said housing, wherein said bubble sensor and said occlusion sensor are both adjacent the narrowest portion of the opposing curved sides, whereby the opposing curved sides at the narrowest portion pre-load the tube improving accuracy across a range of different tube materials and fluid flow in the tube is monitored for bubbles and occlusions.

2. A compact sensor for detecting bubbles and occlusions as in claim 1 wherein:

said occlusion sensor comprises a thin film pressure sensor.

3. A compact sensor for detecting bubbles and occlusions as in claim 2 wherein:

the thin film pressure sensor comprises a strain gauge.

4. An integrated compact sensor for detecting bubbles in a fluid flow and occlusions in a tube comprising:

a housing having opposing curved sides forming a channel adapted to receive and pre-load the tube, said channel having a narrowest portion;

a base connecting the opposing curved sides;

an opening formed in said base between the opposing curved sides and adjacent the narrowest portion of said channel;

a pressure sensor load button placed in said opening adjacent the narrowest portion of said channel;

a sensor coupled to said pressure sensor load button, whereby a force received by said pressure sensor load button is measured by said sensor;

an ultrasonic transmitter placed adjacent one of the opposing curved sides of said housing; and an ultrasonic receiver placed adjacent the other one of the opposing curved sides of said housing, and wherein said ultrasonic transmitter and said ultrasonic receiver and said pressure sensor load button are each adjacent the narrowest portion of the opposing curved sides forming said channel, whereby the narrowest portion of the opposing curved sides pre-load the tube improving accuracy across a range of different tube materials and electrical signals from said sensor and said ultrasonic transmitter and receiver are used to detect bubbles in the fluid flow and occlusions in the tube.

5. An integrated compact sensor for detecting bubbles in a fluid flow and occlusions in a tube as in claim 4 wherein:

said sensor comprises a thin film strain gauge.

6. An integrated compact sensor for detecting bubbles in a fluid flow and occlusions in a tube as in claim 4 wherein said sensor comprises:

an elongated insert having supported first and second ends with said pressure sensor load button positioned midway between the first and second ends;

a first strain gauge placed between the first end and said pressure sensor load button; and a second strain gauge placed between the second end and said pressure sensor load button, whereby a pressure exerted by the tube on said pressure sensor load button causes a stress in said first and second strain gauges resulting in a signal proportional to the pressure.

7. An integrated compact sensor for detecting bubbles in a fluid flow and occlusions in a flexible tube comprising:

a housing having opposing curved sides forming a channel having a narrowest portion, the narrowest portion of the channel having a predetermined fixed width adapted to receive the flexible tube;

an elongated base attached to the housing and connecting the opposing curved sides of the channel;

an opening formed in said base between the opposing sides of said channel, and adjacent the narrowest portion of the channel;

a pressure sensor load button placed in said opening and extending into said channel between the opposing curved sides;

sensor supports formed in said elongated base on either side of said opening formed in said base;

a pressure sensor insert extending between and supported by said sensor supports adjacent said pressure sensor load button;

a first and second strain gauge sensor formed on said pressure sensor insert, one each of said first and second strain gauge sensors placed between one of said sensor supports and said pressure sensor load button, whereby said pressure sensor load button is positioned between said first and second strain gauge sensors stressing said first and second strain gauge sensors when a pressure is applied to said pressure sensor load button;

an ultrasonic transmitter placed adjacent one of the opposing curved sides of said channel in said housing;

an ultrasonic receiver placed adjacent the other one of the opposing curved sides of said channel in said housing; and wherein said pressure sensor load button, said ultrasonic transmitter and said ultrasonic receiver are each adjacent the narrowest portion of the opposing curved sides, whereby electrical signals from said first and second strain gauge sensors are used to detect bubbles in the fluid flow and signals from said ultrasonic transmitter and receiver are used to detect occlusions in the tube.

8. A method of detecting bubbles in fluid flow and occlusions in a tube comprising the steps of:

placing a tube carrying a fluid in a curved channel having a bottom and a width with a narrowest portion in a housing so as to provide the tube with a predetermined pre-compression at the narrowest portion;

transmitting ultrasound adjacent one side of the tube within the curved channel;

receiving the transmitted ultrasound adjacent an opposing side of the tube within the curved channel;

processing a received ultrasound signal, whereby a bubble in the fluid flow can be detected;

positioning a sensor load button at the bottom of the curved channel and adjacent the narrowest portion;

contacting the sensor load button adjacent the tube between sides of the curved channel and adjacent the narrowest portion;

coupling a strain gauge to the sensor load button; and processing a signal from the strain gauge proportional to a pressure placed on the sensor load button, whereby an occlusion in the tube can be detected, whereby both bubbles in fluid flow and occlusions in the tube are detected with the received ultrasound signal and the sensor load button adjacent the narrowest portion of the housing.

* * * * *